(12) United States Patent
Nagy et al.

(10) Patent No.: US 10,046,311 B2
(45) Date of Patent: Aug. 14, 2018

(54) POST TREATED SILVER CATALYSTS FOR EPOXIDATION

(71) Applicant: Lyondell Chemical Technology, L.P., Houston, TX (US)

(72) Inventors: Sandor Nagy, Seabrook, TX (US); Barbara Kimmich, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/217,564

(22) Filed: Jul. 22, 2016

(65) Prior Publication Data

US 2017/0021337 A1  Jan. 26, 2017

Related U.S. Application Data

(60) Provisional application No. 62/196,503, filed on Jul. 24, 2015.

(51) Int. Cl.

| | | |
|---|---|---|
| *B01J 23/00* | (2006.01) | |
| *B01J 23/06* | (2006.01) | |
| *C07D 301/10* | (2006.01) | |
| *B01J 23/68* | (2006.01) | |
| *B01J 23/62* | (2006.01) | |
| *B01J 23/652* | (2006.01) | |
| *B01J 23/656* | (2006.01) | |
| *B01J 23/66* | (2006.01) | |
| *B01J 37/02* | (2006.01) | |
| *B01J 23/89* | (2006.01) | |

(52) U.S. Cl.
CPC .......... *B01J 23/686* (2013.01); *B01J 23/002* (2013.01); *B01J 23/007* (2013.01); *B01J 23/62* (2013.01); *B01J 23/6525* (2013.01); *B01J 23/6567* (2013.01); *B01J 23/66* (2013.01); *B01J 23/687* (2013.01); *B01J 23/688* (2013.01); *B01J 23/896* (2013.01); *B01J 23/8946* (2013.01); *B01J 37/0201* (2013.01); *B01J 37/0236* (2013.01); *C07D 301/10* (2013.01); *B01J 2523/00* (2013.01)

(58) Field of Classification Search
CPC ... B01J 23/66; B01J 23/68; B01J 23/62; B01J 23/652; B01J 23/656; B01J 21/00; B01J 23/686; B01J 23/688; B01J 23/6525; B01J 23/6567; B01J 23/002; B01J 23/007; B01J 23/8946; B01J 23/896; B01J 2523/00; C07D 301/10; C07D 301/0201
USPC .......................... 502/183, 184, 305; 549/534
See application file for complete search history.

(56) References Cited

U.S. PATENT DOCUMENTS

| | | | | |
|---|---|---|---|---|
| 4,033,903 A | * | 7/1977 | Maxwell ................ | B01J 23/66 502/347 |
| 5,703,254 A | | 12/1997 | Gaffney et al. | |
| 5,864,047 A | * | 1/1999 | Gaffney ................ | B01J 23/688 549/536 |

OTHER PUBLICATIONS

International Search Report and Written Opinion for PCT/US2016/043661 dated Oct. 20, 2016.

\* cited by examiner

*Primary Examiner* — Taylor V Oh

(57) ABSTRACT

The present disclosure generally relates to a silver-based epoxidation catalyst. In certain embodiments, a method is provided for modulating the reactivity of the silver-based epoxidation catalyst, comprising the catalyst being post-treated with at least two different salt solutions. In some embodiments, the treatment results in the deposition of one or more metals onto the surface of the catalyst. In further embodiments, method is also provided of using the silver catalyst to generate an epoxide from an olefin.

10 Claims, No Drawings

POST TREATED SILVER CATALYSTS FOR EPOXIDATION

CROSS-REFERENCE TO RELATED APPLICATIONS

This application claims the benefit of priority to U.S. Provisional Application No. 62/196,503, filed on Jul. 24, 2015, which is incorporated herein by reference in its entirety.

BACKGROUND OF THE INVENTION

I. Field of the Invention

The present disclosure relates to epoxidation catalysts and methods. In some embodiments, the present disclosure relates to catalysts which may be used in the production of epoxides from olefins. In some aspects, the present disclosure also provides methods of using the catalysts to generate an epoxide.

II. Description of Related Art

The epoxidation of olefins with silver catalysts is an industrially useful process for preparing such compounds as ethylene oxide and propylene oxide. The use of silver catalysts with molecular oxygen and a terminal alkene or aralkene produce the corresponding epoxide. The introduction of alkali metals including potassium has been shown to improve the efficacy of these silver catalysts. While the introduction of potassium and other alkali metals has been shown to increase catalytic efficiency, post-treatment of the catalyst with other salts, such that other metals are deposited onto the catalyst, could further enhance the activity or efficacy of the catalyst. The present disclosure provides new catalysts which have been post-treated with two metal salts and are useful for the epoxidation of olefins.

SUMMARY OF THE INVENTION

In one aspect, the present disclosure provides a catalyst comprising:
A) from about 10 wt % to about 70 wt % of silver;
B) from about 0.0 wt % to about 5.0 wt % of a promoter selected from the groups consisting of rhenium, tungsten, zinc, nickel, gold, copper, scandium, ytterbium, sodium, potassium, lithium, rubidium, cesium, and molybdenum;
C) from about 30 wt % to about 90 wt % of a solid component selected from calcium titanate, magnesium titanate, barium titanate, strontium titanate, calcium carbonate, magnesium carbonate, barium carbonate, or strontium carbonate; and
D) from about 0.1 wt % to about 6.5 wt % of a salt mixture comprising a first salt and a second salt, wherein the first salt is a Group 1 salt and the second salt is gallium, silver, gold, calcium, barium, strontium, or magnesium salt, and wherein the salt mixture coats the silver, the solid support, or the promoter.

In some embodiments, the promoter is molybdenum, zinc, or rhenium. In some embodiments, the solid component is calcium carbonate. In some embodiments, the first salt comprises from about 0.05 wt % to about 4.0 wt % of the catalyst. In some embodiments, the second salt comprises from about 0.05 wt % to about 2.5 wt % of the catalyst. In some embodiments, the silver comprises from about 30 wt % to about 60 wt % of the catalyst. In some embodiments, the solid component comprises from about 45 wt % to about 65 wt % of the catalyst. In some embodiments, the catalyst further comprises an inert support.

In another aspect, the present disclosure provides a method of preparing a catalyst comprising:
A) obtaining a solid component on which silver has been deposited comprising from about 10 wt % to about 70 wt % silver and optionally further comprises a promoter deposited on the solid component;
B) contacting the solid component of step A) with a first salt and a second salt, wherein the first salt is a Group 1 salt and the second salt is selected from gallium, silver, gold, calcium, barium, strontium, and magnesium salt under conditions sufficient to cause deposition of both metals; and
C) depositing from about 0.05 wt % to about 2.5 wt % of the second salt and about 0.05 wt % to about 4.0 wt % of the first salt onto the solid component.

In some embodiments, the second salt is selected from gold chloride, potassium nitrate, silver nitrate, gallium nitrate, barium nitrate, magnesium nitrate, strontium nitrate, and calcium nitrate. In some embodiments, the first salt is selected from potassium carbonate and potassium nitrate. In some embodiments, the solid component comprises from about 0.05 wt % to about 4.0 wt % of the first salt deposited on the solid component. In some embodiments, the solid component comprises from about 0.05 wt % to about 2.0 wt % of the second salt deposited on the solid component. In some embodiments, the solid component comprises from about 30 wt % to about 60 wt % of silver deposited on the solid component. In some embodiments, the silver deposited onto a solid component further comprises a promoter. In some embodiments, the promoter is selected from rhenium, tungsten, zinc, nickel, gold, copper, scandium, ytterbium, sodium, potassium, lithium, rubidium, cesium, and molybdenum. In some embodiments, the promoter is selected from molybdenum, zinc, and rhenium. In some embodiments, the promoter is present from about 0 wt % to about 5 wt %. In some embodiments, the deposition of the first salt and the second salt comprises a post-treatment step after the promoter has been incorporated into the silver deposited onto a solid component. In some embodiments, step B) further comprises reacting the solid component under conditions sufficient to cause a chemical reduction of the deposited silver to elemental silver. In some embodiments, the catalyst is dried at a temperature from about 100° C. to about 200° C. In some embodiments, the catalyst is calcinated at a temperature from about 250° C. to about 500° C. In some embodiments, the catalyst further comprises an inert support.

In yet another aspect, the present disclosure provides a catalyst prepared by the method disclosed herein. In some embodiments, the second salt is selected from gold chloride, potassium nitrate, silver nitrate, gallium nitrate, barium nitrate, magnesium nitrate, strontium nitrate, and calcium nitrate. In some embodiments, the first salt is selected from potassium carbonate and potassium nitrate. In some embodiments, the catalyst comprises from about 0.05 wt % to about 4.0 wt % of the first salt. In some embodiments, the catalyst comprises from about 0.05 wt % to about 2.0 wt % of the second salt. In some embodiments, the catalyst comprises from about 30 wt % to about 60 wt % of silver. In some embodiments, the silver deposited onto a solid component further comprises a promoter. In some embodiments, the promoter is selected from rhenium, tungsten, zinc, nickel, gold, copper, scandium, ytterbium, sodium, potassium, lithium, rubidium, cesium, and molybdenum. In some embodiments, the promoter is selected from molybdenum, zinc, and rhenium. In some embodiments, the catalyst comprises from about 0 wt % to about 5 wt % of the promoter. In some embodiments, the deposition of the first salt and the second salt comprises a post-treatment step after the promoter has been incorporated into the silver deposited onto a solid component. In some embodiments, step B) further comprises reacting the solid component under conditions sufficient to cause a chemical reduction of the deposited silver to elemental silver. In some embodiments, the catalyst is dried at a temperature from about 100° C. to about 200° C. In some embodiments, the catalyst is calcinated at a temperature from about 250° C. to about 500° C. In some embodiments, the catalyst further comprises an inert support.

In yet another aspect, the present disclosure provides a method of epoxidizing an alkene$_{(C \leq 12)}$ or aralkene$_{(C \leq 12)}$ in the presence of oxygen and a catalyst of the present disclosure to produce an epoxide$_{(C \leq 12)}$.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

DESCRIPTION OF ILLUSTRATIVE EMBODIMENTS

In some aspects, the present disclosure provides a silver catalyst which is treated with a potassium salt and another metal salt. In some embodiments, the other metal salt is a metal nitrate salt. In some embodiments, the mixture of metal salt and potassium salt results in a metal being deposited on the catalyst surface. The present disclosure also provides methods of using these catalysts for the epoxidation of terminal alkenes and aralkenes.

I. Silver Epoxidation Catalyst

In some aspects, the present disclosure provides an epoxidation catalyst wherein silver is deposited on a solid component and the solid component with deposited silver is treated with two or more metal salts. In some aspects, the treatment of the catalyst includes at least one salt that contains a nitrate anion and at least one salt that contains a Group 1 metal cation such that the salts deposit a metal onto the solid component. The catalyst of the present disclosure may be used in an epoxidation reaction to produce epoxide from an alkene or aralkene.

In some aspects, the present disclosure is an epoxidation catalyst with silver deposited on a solid component. A wide variety of potential solid components may be used with deposited silver including but not limited to Group 2 metal carbonates or Group 2 metal titanates. Additionally, other solid components upon which the silver catalyst of the present disclosure can be prepared include those described in U.S. Pat. Nos. 5,525,741; 5,861,519 and 5,864,047; U.S. Pat. App. Pub. Nos. 2005/0027134 and 2012/0277446; and WIPO Pat. App. Pub. Nos. WO 2004/030813; WO 2004/039496; and WO 2011/074508. In some embodiments, the solid component is a Group 2 metal carbonate. Some non-limiting examples of Group 2 carbonates include magnesium carbonate, calcium carbonate, strontium carbonate, and barium carbonate. In other embodiments, a Group 2 metal titanate is used as the solid component. In some embodiments, a mixture of the solid component comprises a mixture of one or more type of solid component including, for example, a mixture of two or more different metal carbonates. In some embodiments, the solid component is deposited on the surface of a suitable inert support, like an alumina, a silica, a zeolite, or a solid form of carbon, or any other suitable inert support(s). In some embodiments, the solid component further comprises an inert support selected from silica, silicates, alumina, aluminates, carbon, carbonates, carbides, diatomaceous earth, silicon carbide, zirconia, magnesia, silica-alumina, silica-magnesia, silica-titania, alumina-titania, alumina-magnesia, alumina-zirconia, thoria, silica-titania-zirconia, and various clays. In other embodiments, the inert support is selected from glass wool, quartz, carborundum, and ion-exchange zeolites. In some embodiments, the catalysts of the present disclosure further comprise any inert support known in the art. Such inert supports for catalysts are well known to a person of skill in the art. In some embodiments, an inert support is a support which does not react with any of the reactants or the final products and the support does not significantly reduce the amount or purity of the final product produced in the reaction. In some embodiments, the catalyst is dried at a temperature from about 100° C. to about 200° C. In some embodiments, the catalyst is calcinated at a temperature from about 250° C. to about 500° C.

In some aspects, when the solid component is a Group 2 metal carbonate, the catalyst can be prepared using a variety of methods known for processing Group 2 metal carbonate including but not limited to extrusion or molding.

In some embodiments, the solid component can adopt a wide variety of different crystal forms, symmetries, or shapes. In some embodiments, the crystal form, symmetry, or shape of the solid component can affect the efficacy of the catalyst.

In an epoxidation catalyst of the present disclosure, the solid component has been doped or deposited with silver. In some embodiments, the source of the silver is a wide variety of different silver salts. In some non-limiting examples, the source of the silver is a silver oxide or as a salt such as silver nitrate, silver carbonate, or silver carboxylate such as a silver oxalate, silver acetate, silver citrate, silver malonate, or a silver fatty acid complex. Additional silver sources include but are not limited to those described in U.S. Pat. No. 5,861,519. In some embodiments, the source of the silver is silver oxide. In other embodiments, the source of the silver is a silver carboxylate. In further embodiments, the source of the silver is silver oxide with one or more stabilizing or complexing agent. In some embodiments, the stabilizing or complexing agent is ethylenediamine and or ethanolamine.

It is contemplated that any method of depositing silver onto a solid may be used to produce an epoxidation catalyst of the present disclosure. In some embodiments, silver is impregnated into the solid component by dissolving the silver into a solvent and/or with a complexing or solubilizing agent is added to the reaction mixture. The solid component is then added to the silver solution until a paste or slurry is formed. The paste or slurry is then dried and calcined in an oven or furnace. In some embodiments, the paste or slurry is dried at a temperature from about 80° C. to about 200° C. In some embodiments, the temperature is from about 100° C. to about 120° C. In some embodiments, drying the paste or slurry requires keeping the temperature elevated for a time period from about 15 minutes to about 12 hours. In some embodiments, the time period is from about 30 minutes to about 6 hours. In some embodiments, the time period is about 1 hour. Calcining the slurry or paste requires a temperature from about 200° C. to about 800° C. for an additional time period for about 10 minutes to about 6 hours. In some embodiments, the calcination is from about 1 hour to about 4 hours. In some embodiments, the drying and calcining of the impregnated silver results in the silver being reduced to its elemental form as well as also removes the volatile compounds from the silver complex. Additionally, in other embodiments, the solution used to impregnated silver is sprayed onto the solid component and then evaporated.

Additional methods of depositing silver onto the catalyst include vapor deposition as well as chemical reduction using a reducing agent to convert silver ions into elemental silver. A wide variety of chemical reducing agents may be used to reduce the silver ions into their ground state. Some of these solvents, solubilizing and complexing agents are described in U.S. Pat. Nos. 5,861,519; 5,856,534 and 7,585,987; U.S. Pat. App. Pub. No. 2012/0277446; and WIPO Pat. App. Pub. No. WO 2011/074508. Non-limiting examples of chemical reduction agents which may be used to reduce silver into its metallic ground state include sugars such as glucose, fructose, and galactose, aldehydes such as formaldehyde, phenylaldehyde, and acetaldehyde, hydrazines such as hydrazine per se, methyl hydrazine, and phenylhydrazine, and metal hydrides such as sodium hydride, lithium hydride, potassium hydride, and calcium hydride, boron compounds such as boron hydride, sodium borohydride, lithium borohydride, and dimethylamineborane, and phosphoric acid based compounds such as sodium hypophosphite and potassium hypophosphite. Other reducing agents which may be used in the present disclosure include those described in U.S. Pat. No. 5,861,519; U.S. Pat. App. Pub. No. 2012/0277446; and WIPO Pat. App. Pub. No. WO 2011/074508. In other embodiments, a reducing gas may be used to reduce the silver to its metallic form. In some non-limiting examples, the reducing gas includes hydrogen, carbon monoxide, methane, ethane, ethylene, propylene, butadiene, or a mixture thereof. It is also contemplated that the silver may be introduced to the solid component with potassium or other salts to impregnate silver into the solid component using "sequential" or "consecutive" methods. These methods can be used to dry off the solvent under reduced pressure and then dried in an oven as well as used to include other metal promoters and potassium salts in the silver solution. In some embodiments, a consecutive method which incorporates an additional transition metal promoter into the solution is used to produce a silver catalyst which contains an additional transition metal promoter.

In some embodiments, the amount of silver deposited on the solid component is from about 10 wt % to about 90 wt %. In additional embodiments, the amount of silver deposited is from about 20 wt % to about 70 wt %. In further embodiments, the amount of silver deposited is from about 30 wt % to about 60 wt %. In certain embodiments, the amount of silver deposited is from about 50 wt % to about 60 wt %. In still further embodiments, the amount of silver deposited is from about 30 wt % to about 40 wt %.

In some aspects, a wide variety of solvents and complexing agents are useful in producing a silver impregnation solution. The solvents and complexing agents which may be used to produce a silver solution include but are not limited alcohols, amines, and carboxylic acids. In further embodiments, the alcohols include polyols such as ethylene glycol or other glycols. In additional embodiments, the amines include ethanolamine, ethylenediamines, methylamine, dimethylamine, or other hydroxyl substituted alkylamines, alkylamines, or alkyldiamines. In certain embodiments, the carboxylic acids include lactic acid, oxalic acid, or ethylenediaminetetraacetic acid. In additional embodiments, the silver is dissolved in a solvent selected from ethanolamine, water, and ethylenediamine.

In some aspects, the silver epoxidation catalyst comprises an additional metal promoter or activator. In further embodiments, the additional metal promoter or activator is deposited on the solid component concurrently with the silver. In other embodiments, the additional metal promoter or activator is deposited on the solid component after the deposition of the silver. It is contemplated that any method of depositing a metal onto the solid component may be used to deposit the additional metal promoter.

A wide variety of different metals are useful as promoters including but not limited to gold, tungsten, rhenium, tin, zinc, and molybdenum. The use of any commercially available salt of these metals is contemplated for use in the preparation of epoxidation catalysts. In some embodiments, the metal is molybdenum. A wide variety of molybdenum salts are commercially available and can be used to deposit molybdenum onto the solid catalytic support. In certain embodiments, the source of molybdenum is an ammonium, Group 1 metal salt, or Group 2 metal salt of an oxoanionic form of molybdenum. In additional embodiments, the source of molybdenum is potassium molydbate, cesium molybdate, lithium molybdate, or ammonium dimolybdate. In further embodiments, the amount of these transition metal promoters is from about 0 wt % to about 5 wt % of the catalyst. In still further embodiments, the promoter amount is from about 0.0 wt % to about 2.5 wt % of the catalyst. In some embodiments, the amount of the promoter is from about 0.05 wt % to about 2.0 wt % of the catalyst. In certain embodiments, the amount of the promoter is from about 0.1 wt % to about 1.0 wt % of the catalyst. In additional embodiments, the amount of the promoter is from 0.25 wt % to about 0.5 wt % of the catalyst.

In another aspect, the epoxidation catalyst also comprises a first salt that is added to the solid component. In some embodiments, the first salt is a Group 1 metal. In some embodiments, the first salt is a potassium salt. The deposition of potassium may be achieved through any known procedure which results in potassium being deposited onto the solid component. In one embodiment, a potassium salt such as potassium nitrate is used. Again, the first metal may be deposited concurrently or after the silver deposition. In some embodiments, the amount of first metal is important to optimizing reaction conditions and efficacy. Furthermore, the amount of potassium is also modified based upon reaction conditions of the epoxidation method. Such optimization is routine for one of skill in the art. In some embodiments, the amount of the first salt deposited onto the catalyst is from about 0.1 wt % to about 6.5 wt %. In certain embodiments, the amount of the first salt is from about 0.25 wt % to about 5.0 wt %. In additional embodiments, the amount of the first salt is from about 0.25 wt % to about 4.0 wt %. In further embodiments, the amount of the first salt is from about 0.25 wt % to about 3.5 wt %. A variety of different solvents may be used to deposit the potassium salt onto the solid component including water or an alcohol such as methanol, ethanol, or propanol.

As described in this disclosure, the addition of a mixture of two or more metal salts to the solid component may also improve the efficacy of the epoxidation catalyst. In some aspects, the mixture of the metal salts includes a variety of different metal salts including metal or metalloid salts. In further embodiments, the metal salts are selected from metal carboxylates, carbonates, nitrates, or halides. In additional embodiments, the metal salt is potassium carbonate. In some embodiments, the metal salts include a Group 2 metal such as strontium, barium, magnesium, and calcium; a coinage metal such as copper, silver, and gold; and a Group 12 or Group 13 metal such as gallium. In other embodiments, the metal is a Group 1 metal such as potassium, lithium, and sodium. In further embodiments, the metal is a transition metal such as tungsten, molybdenum, tin, vanadium, tellurium, titanium, gallium, chromium, zirconium, nickel, palladium, platinum, silver, gold, copper, rhenium, rhodium, and zinc.

In some aspects, a wide range of methods can be employed to deposit these metals onto the catalyst. In some embodiments, the catalyst is suspended in a solvent to which the first metal salt is added. In further embodiments, this slurry is mixed for a time period from about 1 minute to about 1 hour before the addition of a second metal salt. In additional embodiments, the time period is about 10 minute to about 30 minutes. The solution after the addition of the second metal salt is in some embodiments, mixed for a time period from about 1 minute to about 1 hour. In certain embodiments, the time period is from about 10 minutes to about 30 minutes. In further embodiments, the solvent is an alcohol or water. In still further embodiments, the solvent is water.

In some aspects, the present disclosure provides for any appropriate methods which can effect deposition of the metal salts on the solid component. In one embodiment, the metal salts are deposited by removing the solvent. In some embodiments, the solvent is removed under elevated temperature. In some embodiments, the solvent is removed under reduced pressure. In other embodiment, the deposition occurs by choice of an insoluble combination of a cation and an anion pair in the solvent. The selection of such would be dependent upon the solvent and the desired metal to be deposited. The choice of insoluble ion pairs for a given solvent would be routine for a person of skill in the art.

In some embodiments, the first salt and second salt deposit from about 0.1 wt % to about 6.5 wt % of the metal onto the solid component. In certain embodiments, the first salt and second salt deposit from about 0.1 wt % to about 6 wt % of the metal onto the solid component. In further embodiments, the first salt and second salt deposit from about 0.25 wt % to about 5.0 wt % of the metal. In still further embodiments, the first salt and second salt deposit from about 0.25 wt % to about 4.0 wt % of the metal. In additional embodiments, the first salt and second salt deposit from about 0.25 wt % to about 3.5 wt % of the metal.

II. Methods of Epoxidation Using a Silver Catalyst

In some aspects of the present disclosure, the silver catalysts described herein may be used in the production of epoxides using an alkenes and aralkenes. The epoxidation of an alkenes and aralkenes can be achieved using an oxidant including but not limited to molecular oxygen or a peroxide. In certain aspects, the method brings the catalyst into contact with the alkene or aralkene and the oxidant under conditions sufficient to result in at least partial oxidation of the alkene or aralkene to the resultant epoxide. The present disclosure contemplates that any known epoxidation method which utilizes a silver catalyst may be used with the catalyst of the present invention. In some non-limiting examples, epoxidation methods which may be used with the catalyst described in the present disclosure include those described in U.S. Pat. Nos. 5,525,741; 5,703,254 and 5,856,534; U.S. Pat. App. Pub. Nos. 2005/0027134 and 2012/0277446; and WIPO Pat. App. Pub. Nos. WO 2004/039496 and 2011/074508.

In some aspects of the present disclosure, the catalyst may be used in a gas phase epoxidation process, wherein the catalyst is in the solid phase and the other reaction components are in the gas phase. In further embodiments, the epoxidation process is a vapor phase process. In general, the amounts and concentrations of the reactants can be selected from a wide variety of different conditions and ranges. Such ranges can be optimized by a skilled artisan based upon the specific reactor and reaction conditions used to obtain the highest yield of the desired epoxide. In some aspects, the epoxidation reaction is carried out in a wide variety of different reactors. The reactions described in the present disclosure may be used in any known fixed-bed or a fluidized-bed reactor. In some embodiment, the reactor used for the epoxidation reaction of the present disclosure is a fixed-bed reactor. Furthermore, it is contemplated that other reactors may be used to generate an epoxide.

The catalyst of the present disclosure may be useful in the epoxidation of any alkene or aralkene. In some embodiments, it is contemplated that the alkene or aralkene is a terminal alkene or aralkene such that the double bond is between two carbon atoms and one of these carbon atoms is a terminal carbon atom. Some non-limiting examples of terminal alkenes or aralkenes which are contemplated by the present disclosure include ethylene, propylene, 1-butene, 1-pentene, 1-hexene, 1-octene, and styrene. In certain embodiments, the alkene used in the epoxidation reaction is propylene. In additional embodiments, the terminal alkene is propylene and propylene oxide is produced as the desired epoxide. It is contemplated that the epoxidation reaction of the present disclosure comprises adding from about 0.1% to about 60% by volume of the alkene or aralkene to the reaction stream. In some embodiments, the volume of the alkene or aralkene is from about 0.5% to about 50% by volume of the reaction stream. In additional embodiments, the reaction stream comprises a volume of olefin from about 1% to about 30% by volume. In other embodiments, the reaction stream comprises a volume of olefin from about 1% to about 15% by volume.

The reaction conditions sufficient to result in the production of an epoxide in accordance with some embodiments of the present disclosure include heating the reaction to a temperature from about 150° C. to about 350° C. In further embodiments, the temperature is from about 200° C. to about 300° C. In still further embodiments, the temperature is from about 225° C. to about 275° C. In some aspects, the reaction conditions sufficient to result in the production of epoxidation include pressurizing the reaction with a pressure from about 1 atmosphere to about 75 atmospheres. In certain embodiments, the method comprises using a pressure from about 1 atmosphere to about 20 atmospheres relative to atmospheric pressure. In additional embodiments, the pressure is from about 1 atmosphere to about 5 atmospheres relative to atmospheric pressure.

In addition to the catalyst activity, the contact time of the reaction stream with the catalyst is important to the conversion of the alkene or aralkene to the desired epoxide. The contact time can be optimized by a skilled artisan based upon the reactor and other reaction conditions such as concentration of the alkene or aralkene and the oxidant. The contact time of the catalyst, in some embodiments, results in a conversion percentage of the alkene to the appropriate epoxide from about 0.5% to about 90%. In some embodiments, the contact time is sufficient to have a conversion percentage of greater than 5% of the alkene or aralkene. The contact time is affected by the Gas Hourly Space Velocity (GHSV) of the reactor. In certain embodiments, depending on the reaction components and concentrations, the GHSV is from about 500 hr$^{-1}$ to about 10,000 hr$^{-1}$. In additional embodiments, the GHSV is from about 200 hr to about 5,000 hr'.

Other factors including, but not limited, adding additives to the epoxidation process can affect the conversion or selectivity of the oxidant to produce the desired epoxide. Some non-limiting examples of these additives include water, carbon dioxide, nitrogen oxygen compounds, and organic halides. These additives can be added directly to the process feedstock or stream of reagents.

Examples of nitrogen compound which may be used in the epoxidation process include but are not limited to NO, $NO_2$, or other gaseous nitrogen oxygen species as well as other amine containing compounds including but not limited to hydrazine, ammonia, and methyl amine. These compounds may also be used in conjunction with other gaseous compounds such as CO, $CO_2$, $PH_3$, $SO_2$, and $SO_3$. In some embodiments, the epoxidation process further comprises adding NO to the reaction stream. In additional embodiments, the reaction comprises adding from about 1 ppm to about 2000 ppm NO to the reaction stream. In further embodiments, the reaction comprises adding about 10 ppm to about 250 ppm NO to the reaction stream.

Additionally, the epoxidation process can further comprise adding an organic halide to the reaction stream. In some embodiments, the organic halide is a gas at room temperature or the organic halide is gaseous at the temperature and pressure at which the epoxidation reaction is carried out. In certain embodiments, the organic halide used in the epoxidation process described herein is a gas below 100° C. and at atmosphere pressure. Non-limiting examples of the organic halide of the present disclosure include an haloalkane$_{(C\leq12)}$, haloalkene$_{(C\leq12)}$, and haloalkyne$_{(C\leq12)}$. In some embodiments, the halogen atom on the haloalkane$_{(C\leq12)}$, haloalkene$_{(C\leq12)}$, or haloalkyne$_{(C\leq12)}$ is chloride. Some non-limiting examples of organic halides include ethylene dichloride, ethyl chloride, vinyl chloride, methyl chloride, and methylene chloride. Other organic halides which may be used in the epoxidation process include those described in JP Pat. Doc. No. 2008-184456. In some embodiments, the organic halide used as an additive in the epoxidation process is ethyl chloride. The amount of organic halide added to the epoxidation reaction is varied depending on the particular salts being used in the catalyst, the amount of other additives included in the reaction, and the concentration of the alkene or aralkene. It is also envisioned that multiple, different organic halides may be used as additives in the epoxidation reaction. In some embodiments, the organic halide is added to the reaction stream in an amount from about 0.1 ppm to about 2000 ppm. In some embodiments, the amount of organic halide is from about 25 to about 500 ppm. In some embodiments, the amount of organic halide is from about 25 ppm to about 300 ppm.

Additionally, the method of epoxidation, in some embodiments, includes adding $CO_2$ into the reaction stream. In certain embodiments, the amount of $CO_2$ added to the reaction stream is from about 1% to about 60% by volume of the feedstream. In further embodiments, the volume of $CO_2$ is from about 5% to about 50% by volume. In still further embodiments, the volume of $CO_2$ is less than 35% by volume. In additional embodiments, the method does not comprise using $CO_2$ in the epoxidation reaction. The inclusion of $CO_2$ is described, e.g. in U.S. Pat. No. 5,625,084, and has been shown to increase the epoxide selectivity as well as leads to an increase in alkene conversion. In some embodiments, the addition of $CO_2$ leads to a decreased drop in the catalyst activity. In certain embodiments, $CO_2$ is used as the diluent gas.

In some aspects, the epoxidation reaction further comprises an unreactive gas molecule which may be used as a diluent, a carrier, or an inert reaction medium for the epoxidation reaction. This gas is also known as a ballast gas. In some embodiments, the ballast gas is any gas which is inert under the conditions used to epoxidize an alkene or aralkene. In further embodiments, the ballast gas is a hydrocarbon, a noble gas, CO, $CO_2$, or nitrogen gas. In certain embodiments, the ballast gas is methane.

In some embodiments, the method of epoxidation comprises using oxygen as an oxidant in the reactor. It is contemplated that any source of molecular oxygen may be used to in the reactor to provide oxygen for the oxidation of the alkene or aralkene. In further embodiments, the oxygen source is a compound which generates molecular oxygen under the epoxidation conditions. In still further embodiments, the compound which generates molecular oxygen is a gas under epoxidation conditions. In additional embodiments, the atmospheric gas ("air") or pure molecular oxygen can be used. In certain embodiments, the epoxidation process of the present disclosure includes introducing oxygen at about 0.25% to about 15% of the total volume to the reactor. In some embodiments, the aralkene or alkene is introduced to the reaction stream and the catalyst before the introduction of the oxygen. This amount can be varied depending on the source and purity of the oxygen gas as would be apparent to a person of skill in the art. Furthermore, it is important to prevent the buildup of excess oxygen in the reactor and, thus, in some embodiments, the oxygen stream can be pulsed to prevent excess oxygen from building up in the reactor. Additionally, based upon the reactor conditions and the purity of the oxygen, the amount of oxygen used is modulated to reduce the flammability of the reaction mixture.

In another aspect, the catalysts of the present disclosure may be used in an epoxidation process comprising water. In some embodiments, when water is used in the reaction stream, the water is present as steam. When water is used in the epoxidation reaction, the amount of water that may be used is from about 0.01 moles to about 20 moles per mole of propylene. In certain embodiments, the amount of water used is from 0.2 moles to about 10 moles. In further embodiments, the amount of water used is from 0.3 moles to about 8 moles. When water is added to the reaction stream, the amount of water is independent of any water present in the other reaction components such as oxygen or the alkene or aralkene.

III. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

IV. Definitions

When used in the context of a chemical group, "hydrogen" means —H; "hydroxy" means —OH; "oxo" means =O; "carbonyl" means —C(=O)— or —C(O)—; "carboxy" means —C(═O)OH (also written as —COOH or —CO$_2$H); "halo" means —F, —Cl, —Br or —I; and "amino" means —NH$_2$. When used in the context of a chemical group, "carboxylate" means a molecule which contains the group —C(═O)O$^-$ (also written as C(O)O$^-$ or —CO$_2^-$) and the overall charge of the molecule is negative; "nitrate" means a molecule of the formula: NO$_3^-$; "carbonate" means a molecule of the formula: CO$_3^{2-}$; and "halide" means a halogen atom formulated as an anion bearing a single negative charge. Any undefined valency on an atom of a structure shown in this application implicitly represents a hydrogen atom bonded to that atom.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "alkenyl" when used without the "substituted" modifier refers to a monovalent, unsaturated, aliphatic group with a carbon atom at the point of attachment, a linear or branched, cyclo-, cyclic or acyclic structure, at least one nonaromatic carbon-carbon double bond, no carbon-carbon triple bonds, and no atoms other than carbon and hydrogen. The term "alkenediyl," when used without the "substituted" modifier, refers to a divalent, unsaturated, aliphatic group, with two carbon atoms as points of attachment, a linear or branched, cyclo-, cyclic or acyclic structure, at least one nonaromatic carbon-carbon double bond, no carbon-carbon triple bonds, and no atoms other than carbon and hydrogen. The term "alkene" refers to a compound having the formula H—R, wherein R is alkenyl as this term is defined above. A "terminal alkene" refers to an alkene having just one carbon-carbon double bond, wherein that bond forms a vinyl group at one end of the molecule. The term "olefin" refers to an alkene or aralkene as those terms are defined above. In some embodiments, when any of these terms are used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH═CHF, —CH═CHCl and —CH═CHBr, are non-limiting examples of substituted alkenyl groups.

The term "aryl," when used without the "substituted" modifier, refers to a monovalent, unsaturated, aromatic group with an aromatic carbon atom as the point of attachment, wherein carbon atom forms part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. When any of these terms are used with the "substituted" modifier, one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkenyl," when used without the "substituted" modifier, refers to the monovalent group -alkenediyl-aryl, in which the terms "alkenediyl" and "aryl" are each used in a manner consistent with the definitions provided above. The term "aralkene" refers to a compound having the formula H—R, wherein R is aralkenyl as this term is defined above. A "terminal aralkene" refers to an aralkene having just one non-aromatic carbon-carbon double bond, wherein that bond forms a vinyl group at one end of the molecule. When the term is used with the "substituted" modifier, one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkenyls are (3-nitrophenyl)-ethenyl and 4-cyano-4-phenyl-but-1-enyl.

The term "alkali metal" refers to an element from Group 1 of the periodic table. In some embodiments, the term "alkali metal" refers to the elements lithium, sodium, potassium, rubidium, and cesium. The term "alkaline earth metal" refers to an element from Group 2 of the periodic table. In some embodiments, the term "alkaline earth metal" refers to the Group 2 elements such as beryllium, magnesium, calcium, strontium, and barium. The term "transition metal" refers to an element of Groups 3-12 including lanthanides.

The use of the word "a" or "an," when used in conjunction with the term "comprising" in the claims and/or the specification, may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. The term "about," when used in the context of epoxidation process conditions, is used to imply the natural variation of conditions and represents a variation of plus or minus 5% of the measurement. In some embodiments, the variation is plus or minus 1% of the measurement.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "epoxide" refers to a three-membered ring comprising an oxygen atom and two carbon atoms joined by single bonds. An epoxide has the following general formula:

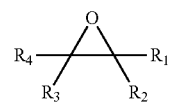

wherein: R$_1$, R$_2$, and R$_3$ are each independently selected from hydrogen, substituted or unsubstituted alkyls; and R$_4$ is selected from hydrogen, substituted or unsubstituted alkyls, or substituted or unsubstituted aryls. An "epoxidation reaction" is a reaction which leads to the generation of an epoxide group in the molecule. The most common epoxidation reaction results from converting an alkene or aralkene functional group within a molecule into an epoxide group.

An "isomer" of a first compound is a separate compound in which each molecule contains the same constituent atoms as the first compound, but where the configuration of those atoms in three dimensions differs.

A "method" is series of one or more steps that lead to a final product, result or outcome. As used herein, the word "method" is used interchangeably with the word "process."

A "solid component" or "carrier" relate to a solid material which is combined with active components of the catalyst. In some aspects, the solid component represents an inert portion of the catalyst. In other aspects, the solid component forms a catalytically active part of the catalyst. In further aspects, the solid component comprises both an inert portion of the catalyst and a catalytically active part of the catalyst. In additional instances, the solid component or carrier can be silica, alumina, organic polymers, or other solid materials with a high surface area and are generally have a high porosity. Additionally, in some embodiments, the solid component or carrier contains numerous pores, voids, or other interstices throughout their structures. In further embodiments, the solid component is a Group 2 carbonate. In some embodiments, the Group 2 metal is calcium. The solid component may be used in any of the multiple available forms including but not limited to granular or powdered. In some embodiments, the solid component is either impregnated with the transition metal precursor or coated with the transition metal precursor.

The above definitions supersede any conflicting definition in any reference that is incorporated by reference herein. The fact that certain terms are defined, however, should not be considered as indicative that any term that is undefined is indefinite. Rather, all terms used are believed to describe the technology in terms such that one of ordinary skill can appreciate the scope and practice the present technology.

V. Examples

The following examples are included to demonstrate certain embodiments of the technology. It should be appreciated by those of skill in the art that the techniques disclosed in the examples which follow represent techniques discovered by the inventors to function well in the practice of the technology, and thus can be considered to constitute modes for its practice. However, those of skill in the art should, in light of the present disclosure, appreciate that many changes can be made in the specific embodiments which are disclosed and still obtain a like or similar result without departing from the spirit and scope of the technology.

Example 1: Catalyst Preparation

Comparative Example 1—1173-131-2 (Ag/Mo/SrTiO$_3$/KNO$_3$)

Preparation of molybdenum modified silver supported on strontium titanate (Ag/Mo/SrTiO$_3$): 11.0 g of oxalic acid dihydrate was slowly added at 50° C. to a stirred mixture of 11 mL of deionized water and 11.0 g of ethylenediamine, followed by 4.06 g of ethanolamine. To the resulting mixture, 0.3 g of ammonium dimolybdate was added, followed by 20.0 g of Ag$_2$O, and the resulting solution was stirred at 50° C. to form a homogeneous solution. 32.0 g of SrTiO$_3$ support was quickly added to the solution resulting in a homogeneous thick paste, which was evenly spread in a calcination dish, and dried for 1 h at 110° C., followed by 4 h of calcination at 300° C.

Post-treatment of molybdenum modified silver supported on strontium titanate by potassium nitrate (Ag/Mo/SrTiO$_3$/KNO$_3$): 4.84 g of the calcined Ag/Mo/SrTO$_3$ precursor from the previous step was suspended in 6 mL of water, then 0.139 g of KNO$_3$ was added to the slurry, stirred for 30 min, and dried in a rotary evaporator under reduced pressure at 60° C., followed by drying in an oven at 110° C. for 2 h.

The nominal composition of the resulting catalyst was: 35.6% Ag; 0.27% Mo and 1.1% K Comparative Example 2—1173-173-1 (Ag/Mo/CaCO$_3$/KNO$_3$)

Preparation of molybdenum modified silver supported on calcium carbonate (Ag/Mo/CaCO$_3$): 21.99 g of oxalic acid dihydrate was slowly added at 50° C. to a stirred mixture of 22 mL of deionized water and 21.6 g of ethylenediamine, followed by 8.05 g of ethanolamine. To the resulting mixture, 0.6 g of ammonium dimolybdate was added, followed by 40.13 g of Ag$_2$O, and the resulting solution was stirred at 50° C. to form a homogeneous solution. 25.92 g of CaCO$_3$ support was quickly added to the solution resulting in a homogeneous thick paste, which was evenly spread in a calcination dish, and dried for 1 h at 110° C., followed by 3 h of calcination at 300° C.

Post-treatment of molybdenum modified silver supported on calcium carbonate by potassium nitrate (Ag/Mo/CaCO$_3$/KNO$_3$): 3.0 g of the calcined Ag/Mo/CaCO$_3$ precursor from the previous step was suspended in 7 mL of water, then 0.045 g of KNO$_3$ was added to the slurry, stirred for 30 min, and dried in a rotary evaporator under reduced pressure at 60° C., followed by drying in an oven at 110° C. for 2 h.

The nominal composition of the resulting catalyst was: 57.9% Ag; 0.43% Mo and 0.57% K Comparative Example 3—1173-145-2 (Ag/Mo/CaCO$_3$/KNO$_3$)

Preparation of molybdenum modified silver supported on calcium carbonate (Ag/Mo/CaCO$_3$): 11.01 g of oxalic acid dihydrate was slowly added at 50° C. to a stirred mixture of 11.09 mL of deionized water, and 11.08 g of ethylenediamine, followed by 3.94 g of ethanolamine. To the resulting mixture, 0.298 g of ammonium dimolybdate hydrate was added, followed by 20.2 g of Ag$_2$O, and the resulting solution was stirred at 50° C. to form a homogeneous solution. 13.68 g of CaCO$_3$ support was quickly added to the solution, resulting in a homogeneous thick paste, which was evenly spread in a calcination dish, and dried 1 h at 110° C., followed by 3 h of calcination at 300° C.

Post-treatment of molybdenum modified silver supported on calcium carbonate by potassium nitrate (Ag/Mo/CaCO$_3$/KNO$_3$): 2.41 g of the calcined Ag/Mo/CaCO$_3$ precursor was suspended in 6 mL of water, then 0.142 g of KNO$_3$ was added to the slurry, stirred for 30 min, and dried in a rotary evaporator under reduced pressure at 60° C., followed by drying in an oven at 110° C. for 2 h.

The nominal composition of the resulting catalyst was: 54.4% Ag; 0.40% Mo and 1.57% K Inventive Example 1—1173-131-3 (Ag/Mo/SrTiO$_3$/Ca(NO$_3$)$_2$+K$_2$CO$_3$)

Post-treatment of molybdenum modified silver supported on strontium titanate by calcium nitrate and potassium carbonate (Ag/Mo/SrTiO$_3$/Ca(NO$_3$)$_2$+K$_2$CO$_3$): 5.0 g of the calcined Ag/Mo/SrTiO$_3$ precursor from the Comparative Example 1 was suspended in 6 mL of water, then 0.0502 g of Ca(NO$_3$)$_2$ tetrahydrate was added to the slurry, and stirred for 15 min. Very slowly, a solution of 0.0293 g of K$_2$CO$_3$ in 1 mL of deionized water was added and stirred for 15 min, then dried in a rotary evaporator under reduced pressure at 60° C., followed by drying in an oven at 110° C. for 2 h.

The nominal composition of the resulting catalyst was: 35.9% Ag; 0.27% Mo and 0.33% K Inventive Example 2—1173-182-2 (Ag/Mo/CaCO$_3$/ Ca(NO$_3$)$_2$+K$_2$CO$_3$)

Preparation of molybdenum modified silver supported on calcium carbonate (Ag/Mo/CaCO$_3$): 11.06 g of oxalic acid dihydrate was slowly added at 50° C. to a stirred mixture of 11.07 mL of deionized water, and 11.02 g of ethylenediamine, followed by 4.1 g of ethanolamine, was added. To the resulting mixture, 0.301 g of ammonium dimolybdate hydrate was added, followed by 20.11 g of Ag$_2$O, and stirred at 50° C. to form a homogeneous solution. 13.48 g of CaCO$_3$ support was quickly added to the solution, resulting in a homogeneous thick paste, which was evenly spread in a calcination dish, and dried for 1 h at 110° C., followed by 4 h of calcination at 300° C.

Post-treatment of molybdenum modified silver supported on calcium carbonate by calcium nitrate and potassium carbonate (Ag/Mo/CaCO$_3$/Ca(NO$_3$)$_2$+K$_2$CO$_3$): 5.0 g of the calcined Ag/Mo/CaCO$_3$ precursor from the previous step was suspended in 7 mL of water, then 0.100 g of Ca(NO$_3$)$_2$ tetrahydrate was added to the slurry, and stirred for 15 min. Very slowly, a solution of 0.0584 g of K$_2$CO$_3$ in 2 mL of deionized water was added and stirred for 15 min, then dried in a rotary evaporator under reduced pressure at 60° C., followed by drying in an oven at 110° C. for 2 h.

The nominal composition of the resulting catalyst was: 56.1% Ag; 0.42% Mo and 0.64% K Inventive Example 3—1173-130-1 (Ag/Mo/CaCO$_3$/ Ba(NO$_3$)$_2$+K$_2$CO$_3$)

Post-treatment of molybdenum modified silver supported on calcium carbonate by barium nitrate and potassium carbonate (Ag/Mo/CaCO$_3$/Ba(NO$_3$)$_2$+K$_2$CO$_3$): 5.0 g of the calcined Ag/Mo/CaCO$_3$ precursor from the Inventive Example 2 was suspended in 7 mL of water, then 0.1098 g of Ba(NO$_3$)$_2$ was added to the slurry, and stirred for 15 min. Very slowly, a solution of 0.0580 g of K$_2$CO$_3$ in 2 mL of deionized water was added and stirred for 15 min, then dried in a rotary evaporator under reduced pressure at 60° C., followed by drying in an oven at 110° C. for 2 h.

The nominal composition of the resulting catalyst was: 56.1% Ag; 0.42% Mo; 1.12% Ba and 0.64% K Inventive Example 4—1173-172-1 (Ag/Mo/CaCO$_3$/ AuCl$_3$+KNO$_3$)

Preparation of molybdenum modified silver supported on calcium carbonate (Ag/Mo/CaCO$_3$): 22.04 g of oxalic acid dihydrate was slowly added at 50° C. to a stirred mixture of 22.0 mL of deionized water and 21.97 g of ethylenediamine, followed by 4.00 g of ethanolamine. To the resulting mixture, 0.61 g of ammonium dimolybdate was added, followed by 40.60 g of Ag$_2$O, and the resulting solution was stirred at 50° C. to form a homogeneous solution. 26.4 g of CaCO$_3$ support was quickly added to the solution, resulting in a homogeneous thick paste which was evenly spread in a calcination dish, which was dried 1 h at 110° C., followed by 4 h of calcination at 300° C.

Post-treatment of molybdenum modified silver supported on calcium carbonate by gold chloride and potassium nitrate (Ag/Mo/CaCO$_3$/AuCl$_3$+KNO$_3$): 2.52 g of the calcined Ag/Mo/CaCO$_3$ precursor from the previous step was suspended in 6 mL of water, then 0.078 g of potassium nitrate was added to the slurry, and stirred for 15 min, followed by the addition of 0.028 g of gold chloride, which was stirred for an additional 15 min then dried in a rotary evaporator under reduced pressure at 60° C., followed by drying in an oven at 110° C. for 2 h.

The nominal composition of the resulting catalyst was: 55.3% Ag; 0.42% Mo; 0.57% Au and 1.85% K Inventive Example 5—1173-172-2 (Ag/Mo/CaCO$_3$/ Ga(NO$_3$)$_3$+KNO$_3$)

Preparation of molybdenum modified silver supported on calcium carbonate (Ag/Mo/CaCO$_3$): 22.04 g of oxalic acid dihydrate was slowly added at 50° C. to a stirred mixture of 22.0 mL of deionized water and 21.97 g of ethylenediamine, followed by 4.00 g of ethanolamine. To the resulting mixture, 0.61 g of ammonium dimolybdate was added, followed by 40.60 g of Ag$_2$O, and the resulting solution was stirred at 50° C. to form a homogeneous solution. 26.4 g of CaCO$_3$ support was quickly added to the solution, resulting in a homogeneous thick paste, which was evenly spread in a calcination dish, and dried 1 h at 110° C., followed by 4 h of calcination at 300° C.

Post-treatment of molybdenum modified silver supported on calcium carbonate by gallium nitrate and potassium nitrate (Ag/Mo/CaCO$_3$/Ga(NO$_3$)$_3$+KNO$_3$): 2.49 g of the calcined Ag/Mo/CaCO$_3$ precursor from the previous step was suspended in 6 mL of water, then 0.153 g of potassium nitrate was added to the slurry, and stirred for 15 min, followed by the addition of 0.023 g of gallium nitrate, and the resulting solution was stirred for an additional 15 min, then dried in a rotary evaporator under reduced pressure at 60° C., followed by drying in an oven at 110° C. for 2 h.

The nominal composition of the resulting catalyst was: 54.9% Ag; 0.41% Mo; 0.24% Ga and 1.62% K.

Comparative Example 4—1181-024-7 (Ag/Re/CaCO$_3$/KNO$_3$)

Preparation of rhenium modified silver supported on calcium carbonate (Ag/Re/CaCO$_3$): 11.0 g of oxalic acid dihydrate was slowly added at 50° C. to a stirred mixture of 11 mL of deionized water and 11.09 g of ethylenediamine, followed by the addition of 3.9 g of ethanolamine. To the resulting mixture, 0.272 g of ammonium perrhenate was added, followed by 20.46 g of Ag$_2$O, and the resulting solution was stirred at 50° C. to form 37 ml of homogeneous solution. 5.3 ml of this silver solution was combined with 2 g of CaCO$_3$ support and mixed into a homogeneous thick paste, which was evenly spread in a calcination dish, and dried 1 h at 110° C., followed by 3 h of calcination at 300° C.

Post-treatment of rhenium modified silver supported on calcium carbonate by potassium nitrate (Ag/Re/CaCO$_3$/ KNO$_3$): 2.4 g of the calcined Ag/Re/CaCO$_3$ precursor from the previous step was suspended in 6 mL of water, then 0.142 g of KNO$_3$ was added to the slurry, and the resulting solution was stirred for 30 min, dried in a rotary evaporator under reduced pressure at 60° C., followed by drying in an oven at 110° C. for 2 h.

The nominal composition of the resulting catalyst was: 57.6 wt % Ag; 0.57 wt % Re and 2.32 wt % K

Comparative Example 5—1173-140-3 (Ag/CaCO3/KNO3)

Preparation of silver supported on calcium carbonate (Ag/CaCO$_3$): 5.5 g of oxalic acid dihydrate was slowly added at 50° C. to a stirred mixture of 5 mL of deionized water and 6.12 g of ethylenediamine, followed by 2.03 g of ethanolamine. To the resulting mixture, 10.0 g of Ag$_2$O was added and stirred at 50° C. The resulting homogeneous solution was combined with 6.7 g of CaCO$_3$ support and mixed into a homogeneous thick paste, which was evenly spread in a calcination dish, and dried 1 h at 110° C., followed by 3 h of calcination at 300° C.

Post-treatment of silver supported on calcium carbonate by potassium nitrate (Ag/CaCO$_3$/KNO$_3$): 2.4 g of the calcined Ag/CaCO$_3$ precursor from the previous step was suspended in 6 mL of water, then 0.142 g of KNO$_3$ was added to the slurry, stirred for 30 min, and dried in a rotary evaporator under reduced pressure at 60° C., followed by drying in an oven at 110° C. for 2 h.

The nominal composition of the resulting catalyst was: 58.2 wt % Ag and 2.27 wt % K

Inventive Example 6—1173-134-1 (Ag/Re/CaCO$_3$/Ca(NO$_3$)$_2$+K$_2$CO$_3$)

Preparation of rhenium modified silver supported on calcium carbonate (Ag/Re/CaCO$_3$): 5.48 g of oxalic acid dihydrate was slowly added at 50° C. to a stirred mixture of 5.52 mL of deionized water and 5.55 g of ethylenediamine, followed by the addition of 2.05 g of ethanolamine. To the resulting mixture, 0.133 g of ammonium perrhenate was added, followed by 10.21 g of Ag$_2$O, and the resulting mixture was stirred at 50° C. The resulting homogeneous solution was combined with 6.8 g of CaCO$_3$ support and mixed into a homogeneous thick paste, which was evenly spread in a calcination dish, and dried for 1 h at 110° C., followed by 3 h of calcination at 300° C.

Post-treatment of rhenium modified silver supported on calcium carbonate by calcium nitrate and potassium carbonate (Ag/Re/CaCO$_3$/Ca(NO$_3$)$_2$+K$_2$CO$_3$): 5.0 g of the calcined Ag/Re/CaCO$_3$ precursor from the previous step was suspended in 7 mL of water, then 0.101 g of Ca(NO$_3$)$_2$ tetrahydrate was added to the slurry, and stirred for 15 min. Very slowly, a solution of 0.0582 g of K$_2$CO$_3$ in 2 mL of deionized water was added and the solution was stirred for 15 min, then dried in a rotary evaporator under reduced pressure at 60° C., followed by drying in an oven at 110° C. for 2 h.

The nominal composition of the resulting catalyst was: 58.3 wt % Ag; 0.56 wt % Re and 0.64 wt % K

Inventive Example 7—1173-141-2 (Ag/CaCO$_3$/(NH$_4$)$_2$Mo$_2$O$_7$+KNO$_3$)

Post-treatment of silver supported on calcium carbonate by ammonium dimolybdate and potassium nitrate (Ag/CaCO$_3$/(NH$_4$)$_2$Mo$_2$O$_7$+KNO$_3$): 3.0 g of the calcined Ag/CaCO$_3$ precursor from Comparative Example 5 was suspended in 5 mL of water, then 0.03 g of ammonium dimolybdate in 3 mL of deionized water was added to the slurry, and stirred for 15 min. 0.1737 g of KNO$_3$ was then added to the slurry and stirred for 15 min, then dried in a rotary evaporator under reduced pressure at 60° C., followed by drying in an oven at 110° C. for 2 h.

The nominal composition of the resulting catalyst was: 58.2 wt % Ag; 0.79 wt % Mo and 2.25 wt % K

Example 2: Catalyst Testing

The catalysts were tested in a 2/8 in stainless steel fixed bed reactor using 1 g of catalyst diluted with 2 g of silicon carbide powder. A continuous flow of 3.0 mol % of propylene and 6.0 mol % of oxygen diluted by nitrogen was applied at 4500 h$^{-1}$ space flow velocity to the catalyst in the presence of 50 ppm of EtCl and NO feed modifiers. The catalyst performance was determined at 2 barg pressure and temperatures of 235° C. and 255° C. after reaching a steady performance. The results are presented in Table 1.

TABLE 1

Results of Epoxidation Based Upon Catalyst Composition

| Example # | Catalyst | Support | Ag nominal wt. % | Modif. comp. before calcination (therm. red. of Ag) | Wt. % mod. metal | First Salt added after calcination | Wt. % mod. metal | Second Salt added after calcination |
|---|---|---|---|---|---|---|---|---|
| Comparateive 1 | 1173-131-2 | SrTiO4 | 36.6 | (NH4)2Mo2O7 | 0.27 (Mo) | KNO3 | 1.1 (K) | |
| Inventive 1 | 1173-131-3 | SrTiO4 | 35.9 | (NH4)2Mo2O7 | 0.27 (Mo) | Ca(NO3)2 | 0.17 (Ca) | K2CO3 |
| Comparateive 2 | 1173-173-1 | CaCO3 | 57.9 | (NH4)2Mo2O7 | 0.43 (Mo) | KNO3 | 0.57 (K) | |
| Inventive 2 | 1173-128-2 | CaCO3 | 56.1 | (NH4)2Mo2O7 | 0.42 (Mo) | Ca(NO3)2 | 0.33 (Ca) | K2CO3 |
| Inventive 3 | 1173-130-1 | CaCO3 | 56.1 | (NH4)2Mo2O7 | 0.42 (Mo) | Ba(NO3)2 | 1.12 (Ba) | K2CO3 |
| Comparative 3 | 1173-145-2 | CaCO3 | 54.4 | (NH4)2Mo2O7 | 0.43 (Mo) | KNO3 | 1.57 (K) | |
| Inventive 4 | 1173-172-3 | CaCO3 | 54.9 | (NH4)2Mo2O7 | 0.41 (Mo) | Ga(NO3)3 | 0.24 (Ga) | KNO3 |
| Inventive 5 | 1173-172-1 | CaCO3 | 55.3 | (NH4)2Mo2O7 | 0.42 (Mo) | AuCl3 | 0.27 (Au) | KNO3 |
| Comparative 5 | 1181-024-7 | CaCO3 | 57.6 | NH4ReO4 | 0.57 (Re) | KNO3 | 2.32 (K) | |
| Inventive 6 | 1173-134-1 | CaCO3 | 58.3 | NH4ReO4 | 0.56 (Re) | Ca(NO3)2 | 0.33 (Ca) | K2CO3 |
| Comparative 6 | 1173-140-3 | CaCO3 | 58.2 | none | n/a | KNO3 | 2.27 (K) | |
| Inventive 7 | 1173-141-2 | CaCO3 | 58.2 | none | n/a | (NH4)2Mo2O7 | 0.79 (Mo) | KNO3 |

| Example # | Wt. % mod. metal | T = 235° C. | | | T = 255° C. | | | |
|---|---|---|---|---|---|---|---|---|
| | | PO Sel., % | PO Prod., lb/qf/h | C3 = Conv % | PO Sel., % | PO Prod., lb/qf/h | C3 = Conv % | |
| Comparateive 1 | | | | | n/a[a] | <0.06[a] | <0.3[a] | [a] 275° C. |
| Inventive 1 | 0.33 (K) | | | | 43.9 | 0.61 | 6.7 | |

TABLE 1-continued

Results of Epoxidation Based Upon Catalyst Composition

| | | | | | | | |
|---|---|---|---|---|---|---|---|
| Comparateive 2 | | 37.9 | 0.63 | 8.3 | 45.3 | 1.56 | 16.7 |
| Inventive 2 | 0.64 (K) | 49.9 | 1.4 | 11.5 | 48.2 | 2.21 | 19.2 |
| Inventive 3 | 0.64 (K) | 41.6 | 1.25 | 14 | 41.7 | 2.11 | 23.1 |
| Comparateive 3 | | 44.9 | 0.85 | 7.4 | 45.5 | 1.48 | 13.1 |
| Inventive 4 | 1.62 | 51.5 | 0.99 | 6.4 | 47.4 | 1.77 | 12.6 |
| Inventive 5 | 1.83 | 46.2 | 0.81 | 7.5 | 45.7 | 1.57 | 14 |
| Comparative 5 | | 41.4 | 1.45 | 17.5 | 43.5 | 2.24 | 26.07 |
| Inventive 6 | 0.64 (K) | 46.3 | 2.43 | 23.0 | 46.1 | 3.8 | 36.9 |
| Comparative 6 | | 43.3 | 2.11 | 20.8 | 44.8 | 3.6 | 44.7 |
| Inventive 7 | 2.25 (K) | 45.8 | 1.31 | 14.3 | 44.6 | 2.02 | 23 |

All of the compounds, complexes, and methods disclosed and claimed herein can be made and executed without undue experimentation in light of the present disclosure. While the compounds, complexes, and methods of this technology have been described in terms of certain embodiments, it will be apparent to those of skill in the art that variations may be applied to the compounds, complexes, and methods, as well as in the steps or in the sequence of steps of the method described herein without departing from the concept, spirit, and scope of the technology. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

U.S. Pat. No. 5,525,741
U.S. Pat. No. 5,625,084
U.S. Pat. No. 5,698,719
U.S. Pat. No. 5,703,254
U.S. Pat. No. 5,763,630
U.S. Pat. No. 5,770,746
U.S. Pat. No. 5,780,657
U.S. Pat. No. 5,856,534
U.S. Pat. No. 5,861,519
U.S. Pat. No. 5,864,047
U.S. Pat. No. 7,585,987
U.S. Pat. App. Pub. No. 2005/0027134
U.S. Pat. App. Pub. No. 2012/0277446
WIPO Pat. App. Pub. No. WO 2004/030813
WIPO Pat. App. Pub. No. WO 2004/039496
WIPO Pat. App. Pub. No. WO 2011/074508
Anderson, N. G., *Practical Process Research & Development—A Guide for Organic Chemists*, $2^{nd}$ ed., Academic Press, New York, 2012.
Brunauer, et al., *J. Am. Chem. Soc.*, 60(2):309-319, 1938.

What is claimed is:

1. A catalyst comprising:
   A) from about 45 to about 65 wt % of silver;
   B) from about 0.0 to about 5.0 wt % of a catalyst promoter selected from the group consisting of molybdenum, tungsten, zinc, nickel, copper, scandium and ytterbium;
   C) from 30 to about 90 wt % of a solid catalyst support selected from the group consisting of calcium titanate, magnesium titanate, barium titanate, strontium titanate, calcium carbonate, magnesium carbonate, barium carbonate, and strontium carbonate; and
   D) from about 0.1 to about 6.5 wt % of a salt mixture comprising from about 0.25 to about 2.5 wt % of a first salt selected from the group consisting of potassium nitrate, silver nitrate, gallium nitrate, barium nitrate, magnesium nitrate, strontium nitrate, and calcium nitrate and from about 0.1 to about 4.0 wt % of a second salt selected from potassium nitrate and potassium carbonate, and wherein the salt mixture coats the silver component of step A), the solid catalyst support, or the catalyst promoter.

2. The catalyst of claim 1, wherein the solid catalyst support is calcium carbonate.

3. A method for producing the catalyst of claim 1 comprising:
   A) obtaining a solid catalyst support on which about 45 to about 65 wt % silver has been deposited, further comprising a catalyst promoter selected from the group consisting of molybdenum, tungsten, zinc, nickel, copper, scandium and ytterbium deposited on the solid catalyst support;
   B) contacting the solid component of step A) with a first salt and a second salt, wherein the first salt is selected from the group consisting of potassium nitrate, silver nitrate, gallium nitrate, barium nitrate, magnesium nitrate, strontium nitrate, and calcium nitrate and the second salt is selected from potassium nitrate and potassium carbonate, in the presence of a solvent selected from the group consisting of water, methanol, ethanol and propanol for achieving the deposition of both metals; and
   C) depositing from about 0.05 to about 2.5 wt % of the second salt and from about 0.05 to about 4.0 wt % of the first salt onto the solid catalyst support.

4. The method of claim 3, wherein the solid catalyst support comprises from about 0.25 to about 2.5 wt % of the first salt deposited on the solid component.

5. The method of claim 3, wherein the catalyst promoter is present at a concentration of from about 0 to about 5 wt %.

6. The method of claim 3, wherein the deposition of the first salt and the second metal salt comprises a post-treatment after the catalyst promoter has been deposited on the silver deposited solid catalyst support.

7. The method of claim 3, wherein step B) further comprises reacting the solid catalyst support with a chemical reducing agent selected from the group consisting of a sugar, aldehyde, hydrazine, metal hydride and phosphite salt to cause a chemical reduction of the deposited silver to elemental silver.

8. The method of claim 3, wherein the catalyst is dried at a temperature of from about 100 to about 200° C.

9. The method of claim 3, wherein the catalyst is calcinated at a temperature of from about 250 to about 500° C.

10. A method comprising reacting an alkene$_{(C\leq 12)}$ or aralkene$_{(C\leq 12)}$ in the presence of oxygen and the catalyst according to claim 1 to produce an epoxide$_{(C\leq 12)}$.

* * * * *

UNITED STATES PATENT AND TRADEMARK OFFICE
CERTIFICATE OF CORRECTION

PATENT NO. : 10,046,311 B2
APPLICATION NO. : 15/217564
DATED : August 14, 2018
INVENTOR(S) : Nagy et al.

Page 1 of 1

It is certified that error appears in the above-identified patent and that said Letters Patent is hereby corrected as shown below:

In the Specification

In Column 4, Line 1, delete "component" and insert -- components --
In Column 4, Line 2, delete "component" and insert -- components --
In Column 4, Line 49, delete "agent." and insert -- agents. --
In Column 5, Line 29, delete "acid" and insert -- acids --
In Column 5, Line 63, after "limited" insert -- to --
In Column 7, Line 19, delete "minute" and insert -- minutes --
In Column 9, Line 6, delete "h'." and insert -- h-1. --
In Column 9, Line 34, delete "atmosphere" and insert -- atmospheric --
In Column 13, Line 8, after "is" insert -- the --
In Column 13, Line 8, delete "lead" and insert -- leads --

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*